US00PP33220P2

(12) United States Plant Patent
Van Swieten

(10) Patent No.: US PP33,220 P2
(45) Date of Patent: Jun. 29, 2021

(54) ***PHALAENOPSIS* ORCHID PLANT NAMED 'PHALHIPVAH'**

(50) Latin Name: ***Phalaenopsis* hybrid**
Varietal Denomination: PHALHIPVAH

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/060,306

(22) Filed: Oct. 1, 2020

(51) Int. Cl.
*A01H 6/62* (2018.01)
*A01H 5/02* (2018.01)

(52) U.S. Cl.
USPC ..... Plt./360

(58) Field of Classification Search
USPC ..... Plt./360
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALHIPVAH', particularly characterized by white, striped flowers with red-purple lips, convex flower shape in lateral view, a medium long and compact plant, and is propagated by meristem tissue culture, is disclosed.

3 Drawing Sheets

Genus and species: *Phalaenopsis* hybrid.
Variety denomination: 'PHALHIPVAH'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHIPVAH'.

The new *Phalaenopsis* plant is a product of a planned breeding program conducted by the inventor in Bleiswijk, the Netherlands. The objective of this breeding program was to create a new *Phalaenopsis* plant with white, striped flowers and red-purple lips, suitable for potted plant production.

The new *Phalaenopsis* plant 'PHALHIPVAH' is a result of cross-pollination made by the inventor in March 2011 in Bleiswijk, the Netherlands, of the proprietary female, or seed parent, *Phalaenopsis* hybrid '01-3554' (unpatented) with the proprietary male, or pollen parent, *Phalaenopsis* hybrid 'PHALBUKAP' (U.S. Plant Pat. No. 25,445).

The new *Phalaenopsis* was selected by the inventor as a single plant within the progeny of the stated cross-pollination in a controlled greenhouse in Bleiswijk, the Netherlands, in March 2014. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019 (Application no. 2019/0995), by Applicant who obtained the subject matter disclosed directly from the inventor. 'PHALHIPVAH' has not been made publicly available or sold anywhere in the world prior to the effective filing date of this application with the exception of sales or disclosures made one year or less before the effective filing date of this claimed invention by Applicant who obtained 'PHALHIPVAH' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHIPVAH' as a new and distinct variety of *Phalaenopsis* plant:

1) White, striped flowers with red-purple lips;
2) Flower shape in lateral view is convex; and
3) Plant is medium long and compact.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in August 2020. Colors in the photographs may differ from the color values cited in the detailed botanical description, which accurately describe the actual colors of the new variety.

DESCRIPTION OF THE NEW VARIETY

Figure 1:
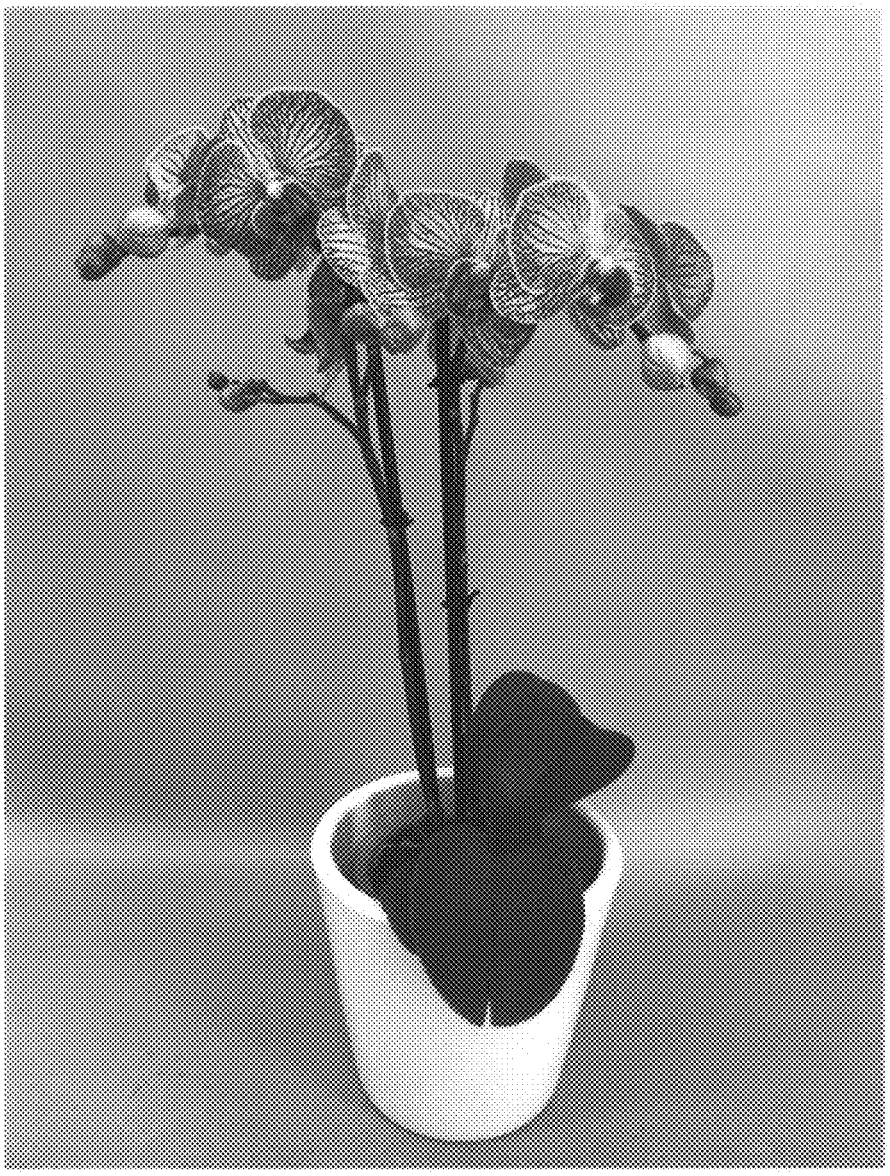
FIG. 1 shows the overall plant habit, including blooms, buds, and foliage of 'PHALHIPVAH'.
Figure 2:
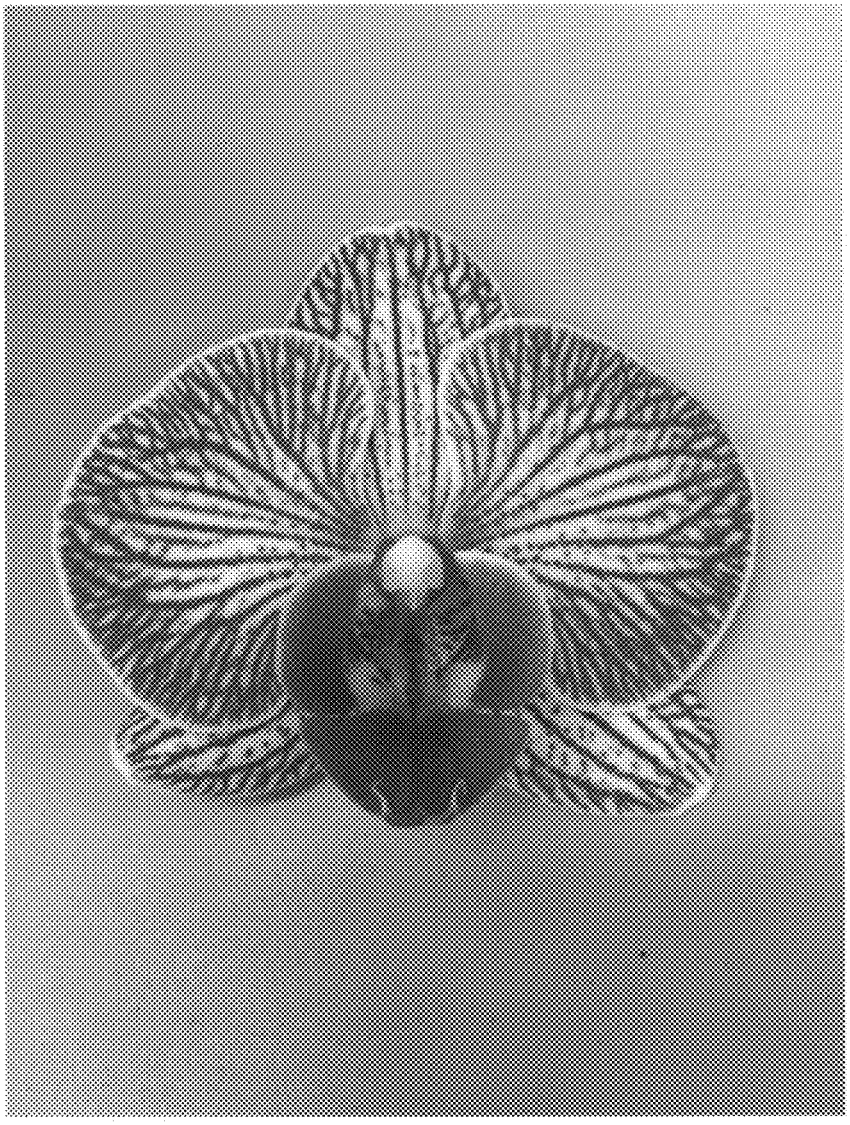
FIG. 2 shows a close-up of a flower of 'PHALHIPVAH'.
Figure 3:
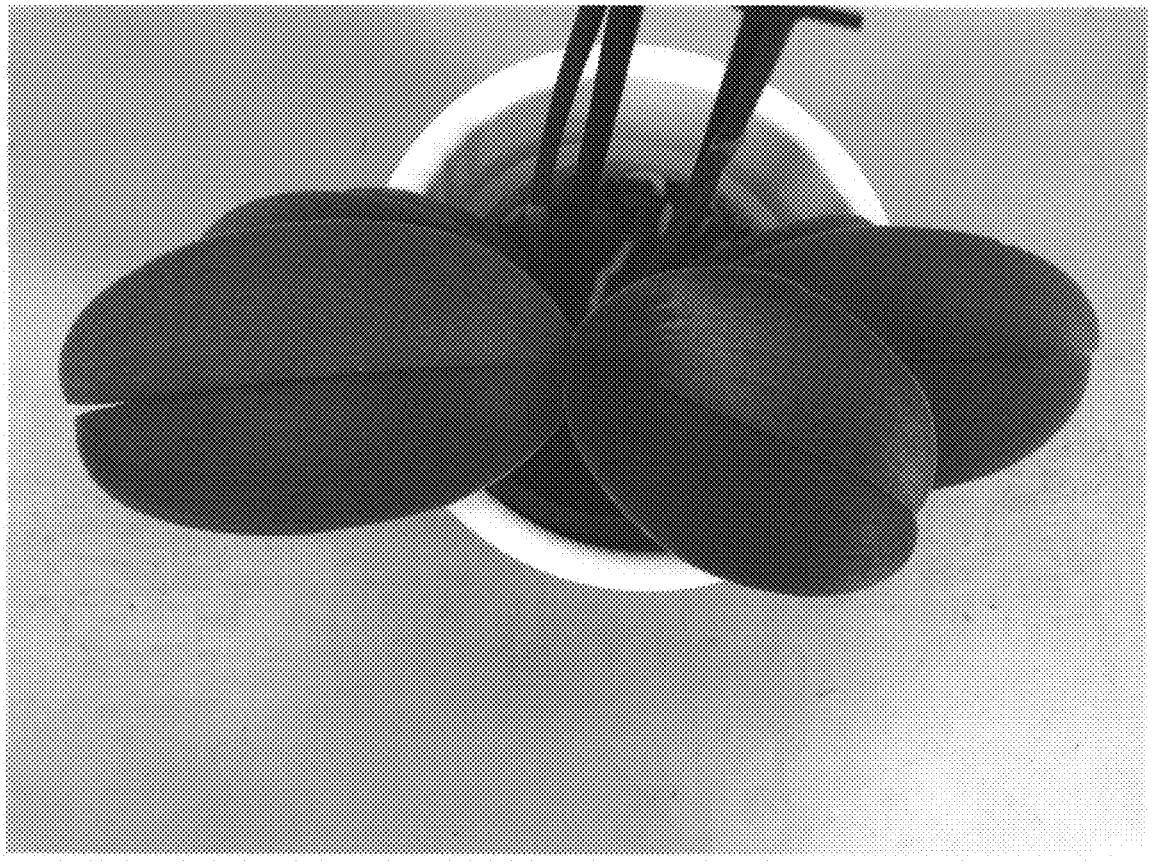
FIG. 3 shows an overhead view of the leaves of 'PHALHIPVAH'.

The following detailed description sets forth the distinctive characteristics of 'PHALHIPVAH'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in August 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHIPVAH'.

Parentage:

*Female parent*.—*Phalaenopsis* cultivar '01-3554' (unpatented).

*Male parent*.—*Phalaenopsis* cultivar 'PHALBUKAP' (U.S. Plant Pat. No. 25,445).

Propagation:

*Type*.—Meristem tissue culture.

Roots:

*Root description*.—Greyed-green (something between RHS 190B and 190C) colored roots with branching lateral roots having yellow-green (something in between RHS 144A and 144B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 34.0 cm to 39.0 cm.

*Width* (*measured from leaf tips*).—About 23.0 cm to 25.0 cm.

*Vigor*.—Strong.

Leaves:

*Mature leaves*.—Quantity per plant: 7 to 8 leaves are produced before flowering. Length (fully expanded): 11.0 cm to 13.0 cm. Width: 6.0 cm to 7.0 cm. Position of the broadest part of the leaf: At the middle. Shape: Oblong. Base shape: Moderately to slightly elongated. Apex: Obtuse to rounded unequal. Leaf blade angle with the petiole (measured from the horizontal position): Between 15 degrees and 30 degrees. Leaf margin: Entire. Color: Upper surface: RHS 147A. Lower surface: RHS 146B. Texture (both upper and lower surfaces): Smooth. Thickness: 2.5 mm to 3.0 mm. Variegation: Absent. Venation: Pattern: Parallel. Color of the midvein: Upper surface: RHS 147A. Lower surface: RHS 146B.

Peduncle:

*Quantity per plant*.—1 to 2.

*Number of flowers per peduncle*.—10 to 15.

*Length*.—34.0 cm to 39.0 cm.

*Diameter*.—3.8 mm to 4.3 mm.

*Strength*.—Strong.

*Aspect*.—Upright to slightly pendent.

*Texture*.—Smooth.

*Color*.—Mix of green (RHS 146C) and brown (RHS 200B).

*Internode length*.—2.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 180.0 mm to 200.0 mm.

*Flowering time*.—First flowers can be expected 10 to 11 months after planting in a 12-cm pot.

*Flower*.—Height: 60.0 mm to 65.0 mm. Diameter: 65.0 mm to 70.0 mm. Depth of lip: 21.0 mm to 23.0 mm.

*Flower longevity*.—On the plant: 10 to 12 weeks.

*Flower shape*.—Convex.

*Fragrance*.—Absent.

*Flower bud*.—Average size: Medium. Length: 18.0 mm to 20.0 mm. Width: 17.0 mm to 19.0 mm. Shape: Egg shaped. Color: Yellow-green (RHS 145C) with a touch of purplish-red (RHS N77B) and few dark purplish-red stripes (RHS N79B).

*Petals*.—Arrangement: Open/free. Shape: Semi-circular. Apex: Rounded to slightly emarginated asymmetric. Margin: Weakly undulated. Length (from base to tip): 29.0 mm to 31.0 mm. Width: 39.0 mm to 41.0 mm. Position of the broadest part of the petal: Toward the base. Color (when fully opened): Upper surface: Basic color: White (RHS NN155C). Over color: Hint of purplish-pink (RHS N78C) at the base; striped (RHS N78A). Lower surface: Basic color: Very light purple (RHS 76B). Over color: Diluting reddish-purple stripes (RHS N78B and N78C). Number of spots, dots, and stripes on the petals (upper surface): Many stripes and few very small dots at the base. Color of spots, dots, and stripes on the petals (upper surface): RHS N78A. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 34.0 mm to 36.0 mm. Width: 29.0 mm to 31.0 mm. Position of the broadest part of the dorsal sepals: At the middle. Color (when fully opened): Upper surface: Basic color: White (RHS NN155C). Over color: Hint of light reddish-purple (RHS N78D) at the base; stripes (RHS N78A). Lower surface: Basic color: Very light purple (something in between RHS 76B and 76C). Over color: Hint of purplish-pink (RHS N78C) at the base and diluting stripes (RHS N78C). Number of spots, dots, and stripes on the dorsal sepals (upper surface): Many stripes and medium very small dots. Color of spots, dots, and stripes on the dorsal sepals (upper surface): RHS N78A. Density of netting of the dorsal sepals (upper surface): None. Color of the netting: Not applicable.

*Lateral sepals*.—Shape: Ovate. Apex: Obtuse asymmetric. Margin: Entire. Length (from base to tip): 35.0 mm to 37.0 mm. Width: 25.0 mm to 27.0 mm. Position of the broadest part of the lateral sepals: Toward the base. Color (when fully opened): Upper surface: Basic color: White (RHS NN155C). Over color: Light yellow-green (something in between RHS 145C and 145D) at the base; stripes (RHS N78A). Lower surface: Basic color: Very light purple (something in between RHS 76B and 76C). Over color: Light yellow-green (RHS 145C) at the base; diluting stripes (RHS N78C). Number of spots, dots, and stripes on the lateral sepals (upper surface): Medium of very small dots and medium to many stripes. Color of spots, dots, and stripes on the lateral sepals (upper surface): Dots (RHS N78A and 61A); stripes (RHS N78A). Density of netting of the lateral sepals (upper surface): None. Color of the netting (upper surface): Not applicable.

*Labellum* (*lip*).—Whiskers: Present. Length of whiskers: 5.0 mm to 7.0 mm. Color of whiskers: Reddish-purple (RHS N78A) with white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 17.0 mm to 19.0 mm. Width: 13.0 mm to 15.0 mm. Color: Upper surface: Hint of greenish-yellow (RHS 5A) and white (RHS NN155C) at the base; red (RHS 185A) on one side; reddish-purple (RHS N78A) toward the other side; white margin (RHS NN155C) at the top. Lower surface: Greenish-white (RHS 155C) at the base and greenish-yellow margin (RHS 5A) on one side; red (RHS 185B) on one side and light purplish-pink (RHS N78C) toward the other side. Number of spots and stripes on the lateral lobe: Few stripes at the base. Color of spots and stripes on the lateral lobe: RHS 185A. Density of netting of the lateral lobe: None. Color of the netting: Not applicable.

*Apical lobe*.—Shape: Triangular. Margin: Entire. Length: 21.0 mm to 23.0 mm. Width: 15.0 mm to 17.0 mm. Color: Upper surface: Greenish-yellow (RHS 5A) at the middle at the base; dark reddish-orange (RHS 175B) at the base and toward wings; reddish-purple (RHS N78A) toward whiskers. Lower surface: Greenish-white (RHS 155C) at the base and at the middle toward whiskers; dark reddish-orange margin (RHS 175B) at the base; greenish-yellow (RHS 1C) toward wings; reddish-purple (RHS N78B) along margin toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small to medium. Height: 6.0 mm to 7.0 mm. Length: 4.0 mm to 5.0 mm. Width: 3.0 mm to 4.0 mm. Color: Greenish-yellow (RHS 5A) on top; light greenish-yellow (something in between RHS 4C and 4D) on sides; dotted (RHS 59A).

Reproductive organs:

*Column*.—Length: 8.0 mm to 10.0 mm. Diameter: 4.0 mm to 5.0 mm. Color: Very light purple (RHS 76B) at the base with few reddish-purple stripes (RHS N78B) and white (RHS NN155C) toward the top.

*Pollinia*.—Quantity: 2. Diameter: 0.9 mm to 1.1 mm. Color: Orange (RHS 24A).

*Ovary*.—Length: 8.0 mm to 10.0 mm. Diameter: 2.1 mm to 2.3 mm.

*Pedicel*.—Length: 26.0 mm to 28 .0 mm. Diameter: 2.4 mm to 2.7 mm. Texture: Smooth. Color: Hint of brown (RHS 200C) at the base; yellow-green (RHS 145C) and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent of 'PHALHIPVAH', cultivar '01-3554' (unpatented), is no longer in existence, therefore a meaningful comparison cannot be made.

'PHALHIPVAH' differs from male parent plant 'PHALBUKAP' (U.S. Plant Pat. No. 25,445) in that 'PHALHIPVAH' has smaller flowers and shorter leaves than 'PHALBUKAP'.

'PHALHIPVAH' is most similar to the commercial *Phalaenopsis* plants named 'PHALFESFI' (U.S. Plant Pat. No. 31,481) and 'PHALDOQAH' (U.S. Plant Pat. No. 27,457). 'PHALHIPVAH' differs from the commercial variety 'PHALFESFI' in that 'PHALHIPVAH' has emarginated dorsal sepal apexes, whereas 'PHALFESFI' has obtuse dorsal sepal apexes. Additionally, 'PHALHIPVAH' has smaller flowers, shorter whiskers, shorter leaves, a shorter plant, and narrower petals than 'PHALFESFI'.

'PHALHIPVAH' differs from the commercial variety 'PHALDOQAH' in that 'PHALHIPVAH' has emarginated dorsal sepal apexes, whereas 'PHALDOQAH' has rounded dorsal sepal apexes. Additionally, 'PHALHIPVAH' has smaller flowers, shorter whiskers, shorter leaves, a shorter plant, and narrower petals than 'PHALDOQAH'.

I claim:

1. A new and distinct variety of *Phalaenopsis* plant named 'PHALHIPVAH', substantially as described and illustrated herein.

* * * * *